(12) United States Patent
Chen et al.

(10) Patent No.: US 10,365,254 B2
(45) Date of Patent: Jul. 30, 2019

(54) ASSESSMENT OF BLOOD COAGULATION USING AN ACOUSTIC RADIATION FORCE BASED OPTICAL COHERENCE ELASTOGRAPHY (ARF-OCE)

(71) Applicant: The Regents of the University of California, Oakland, CA (US)

(72) Inventors: Zhongping Chen, Irvine, CA (US); Jiang Zhu, Irvine, CA (US); Xiangqun Xu, Hangzhou (CN)

(73) Assignee: The Regents of the University of California, Oakland, CA (US)

(*) Notice: Subject to any disclaimer, the term of this patent is extended or adjusted under 35 U.S.C. 154(b) by 255 days.

(21) Appl. No.: 15/293,208

(22) Filed: Oct. 13, 2016

(65) Prior Publication Data

US 2017/0107558 A1   Apr. 20, 2017

Related U.S. Application Data

(60) Provisional application No. 62/241,649, filed on Oct. 14, 2015.

(51) Int. Cl.
| | |
|---|---|
| *G01N 1/00* | (2006.01) |
| *G01N 29/28* | (2006.01) |
| *G01N 29/24* | (2006.01) |
| *G01N 29/06* | (2006.01) |
| *G01N 29/07* | (2006.01) |
| *G01N 29/11* | (2006.01) |
| *G01N 29/12* | (2006.01) |

(52) U.S. Cl.
CPC ......... *G01N 29/28* (2013.01); *G01N 29/0672* (2013.01); *G01N 29/07* (2013.01); *G01N 29/11* (2013.01); *G01N 29/12* (2013.01); *G01N 29/2418* (2013.01); *G01N 2291/011* (2013.01); *G01N 2291/014* (2013.01); *G01N 2291/015* (2013.01); *G01N 2291/017* (2013.01); *G01N 2291/02466* (2013.01); *G01N 2291/02827* (2013.01)

(58) Field of Classification Search
CPC ....................................................... G01N 1/00
See application file for complete search history.

(56) References Cited

U.S. PATENT DOCUMENTS

2005/0148899 A1* 7/2005 Walker ................. A61B 5/0048
600/553

\* cited by examiner

*Primary Examiner* — Jyoti Nagpaul
(74) *Attorney, Agent, or Firm* — Marcus C. Dawes; Daniel L. Dawes

(57) ABSTRACT

An apparatus and method of using an optical coherence elastography (OCE) under acoustic radiation force (ARF) excitation includes the steps of inducing an excitation wave in a blood sample by use of an ultrasound beam from an ultrasonic transducer; measuring an elastic property of the blood sample by use of an optical coherence tomography (OCT) beam transverse to the ultrasound beam to dynamically measure the elastic property of the blood sample during coagulation and assessing the clot formation/dissolution kinetics and strength.

20 Claims, 5 Drawing Sheets
(5 of 5 Drawing Sheet(s) Filed in Color)

Fig. 1a
Fig. 1b
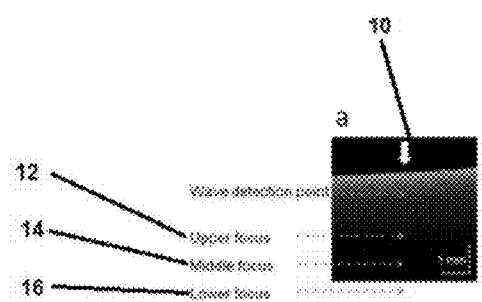
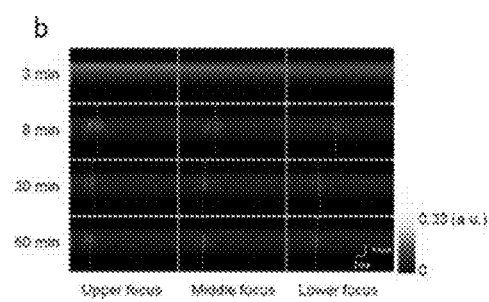

ASSESSMENT OF BLOOD COAGULATION USING AN ACOUSTIC RADIATION FORCE BASED OPTICAL COHERENCE ELASTOGRAPHY (ARF-OCE)

GOVERNMENT SUPPORT

This invention was made with government support under contract 482771-78652, funded by NIH NEI EY-021529; contract 442771-29743, funded by NIH NHLBI HL-125084; and contract 81171378, funded by NSFC. The government has certain rights in the invention.

RELATED APPLICATIONS

This application is related to provisional patent application, entitled, Approach For Assessment Of Blood Coagulation Using An Acoustic Radiation Force Based Optical Coherence Elastography (ARF-OCE) Ser. No. 62/241,649, filed on Oct. 14, 2015, under 35 USC 119, which is incorporated herein by reference.

BACKGROUND

Field of the Technology

The invention relates to the fields of ARF systems and OCE systems and methods of using the same

Description of the Prior Art

Coagulopathy, a condition in which blood coagulation is impaired, can cause life-threatening bleeding or thrombotic disorders resulting from a variety of conditions, including severe trauma, illness or surgery. Dynamic and quantitative assessment of coagulation is important to diagnose potential causes of hemorrhage, to guide hemostatic therapies, and to predict the risk of bleeding during consecutive surgical procedures. During surgery, trauma care and chronic disease management, clinicians often encounter the challenging task of maintaining a precarious balance between bleeding and coagulation. Most commonly, routine laboratory-based coagulation tests, e.g., prothrombin time/International Normalized Ratio (PT), activated partial thromboplastin time (aPTT), fibrinogen levels, and platelet numbers, are being used to assess the patient's current coagulation status. However, the tests are of limited value in perioperative and acutely ill patients because there are delays from sample transportation and centrifugation to obtaining results (45-60 min); the turnaround time is often too long for the tests to be reliable for informing blood transfusion or anti-coagulant therapy in the context of rapidly changing coagulation conditions in critically ill or injured patients. Moreover, the coagulation tests are determined in plasma rather than whole blood: there is no information available on platelet function and red blood cell function.

Abnormal mechanical properties of clots are associated with the risk of thrombosis and bleeding. Thromboelastography (TEG/ROTEM®) has been widely used in a clinical setting for monitoring coagulation during procedures, including hepatic and cardiac surgeries, which are associated with high risk of massive bleeding. However, TEG is not an ideal modality for assessing clot mechanical properties due to its poor sensitivity, repeatability, and lack of standardization. While the poor standardization of TEG may be due to the absence of standard clinical protocols, it may also be related to the physical method of measurement which requires accurate measurement of stress and strain.

Recently, optical methods have been developed for the assessment of the biomechanical properties of clotted blood, such as magnetomotive optical coherence elastography (MMOCE) method and laser speckle rheology (LSR) method due to the high sensitivity. MMOCE method uses fundamental resonant frequency to represent the elastic properties of clotted blood. However, it cannot monitor the dynamic change of the elastic properties during blood coagulation and needs contact between microbead and detected sample for the magnetic force application, which may change the coagulation process. The non-contact LSR method can detect the coagulation process in real-time. However, the speckle autocorrelation time constant used for characterizing the elastic properties in the LSR method cannot directly calculate the elastic modulus without subsequent calibration.

Optical coherence elastography (OCE), employing optical coherence tomography (OCT) to detect depth-resolved sample deformation, has been used to assess tissue biomechanics. OCE techniques offer distinct features in comparison to ultrasound elastography and magnetic resonance elastography (MRE), including imaging spatial resolution, acquisition speed, mechanical sensitivity, and imaging penetration. The spatial resolution of OCE, as set by OCT, is typically 1-10 µm: at least an order of magnitude higher than MRE and ultrasound elastography. Also, the development of OCE using phase-resolved OCT detection can assess and extract different parameters of tissue deformation with high accuracy to reconstruct the tissue biomechanical properties. A recent OCE method based on shear wave measurement can provide the elastic modulus with high spatial resolution and high sensitivity. The shear wave velocity V can be directly used to calculate the shear modulus µ by the following equation:

$$\mu = \rho \cdot V^2 \qquad (1)$$

where $\rho$ is the density of the tissue.

Excitation and detection are generally two characteristics of an OCE system. Various loading approaches have been proposed, such as the use of magnetomotive nanoparticles as the internal transducers for vibration and applying acoustic radiation force for remote stimulation. Using an ultrasonic transducer, ARF can remotely induce a shear wave without the contact in the OCE system. An OCT Doppler variance method for measuring the transverse vibration induced by ARF orthogonal excitation (ARFOE-OCE) was recently developed. The vibration is perpendicular to the OCT beam, and the shear wave propagates along the OCT beam. The shear modulus, indicating tissue stiffness, in a two-layer phantom at the position beyond the OCT imaging depth was accurately measured by the method.

Reliable clot diagnostic systems are needed for directing treatment in a broad spectrum of cardiovascular diseases and coagulopathy.

BRIEF SUMMARY

What is disclosed is a non-contact measurement of elastic modulus for dynamic and quantitative assessment of whole blood coagulation using acoustic radiation force orthogonal excitation optical coherence elastography (ARFOE-OCE). In this system, acoustic radiation force (ARF) is produced by a remote ultrasonic transducer, and a shear wave induced by ARF excitation is detected by the optical coherence tomography (OCT) system. During porcine whole blood coagulation, changes in the elastic property of the clots increase the shear modulus of the sample, altering the propagating velocity of the shear wave. Consequently, dynamic blood coagulation status can be measured quantitatively by relating the velocity of the shear wave with clinically relevant coagulation metrics, including reaction time, clot formation kinetics and maximum shear modulus. The results show that the ARFOE-OCE is sensitive to the clot formation kinetics and can differentiate the elastic properties of the recalcified porcine whole blood, blood added with kaolin as an activator, and blood spiked with fibrinogen.

What is disclosed is the non-contact and real-time measurement of the shear wave velocity and elastic modulus during the dynamic blood coagulation process using the ARFOE-OCE method, where the ARF orthogonal to the OCT beam produces the vibration of the blood tissue and the shear wave propagation is visualized utilizing phase-resolved OCT detection with the Doppler variance method. Doppler variance analysis works better if the vibration direction is perpendicular to the optical detection direction when compared with Doppler phase analysis. We validate the feasibility of ARFOE-OCE for quantitative assessment of the dynamic porcine whole blood coagulation process by temporally tracking induced shear waves. Then we apply this method for differentiating the coagulation process of the recalcified porcine whole blood and the blood added with kaolin as an activator using coagulation metrics, including reaction time, clot formation kinetics and maximum shear modulus. Fibrinogen is a plasma protein that can be transformed into an insoluble fibrin by the action of thrombin in the final stage of the blood coagulation and plays a key role in the hemostatic system. The normal plasma fibrinogen level ranges from 2.0 to 4.5 g/L, while increased plasma fibrinogen concentration can be associated with increased blood coagulability and viscosity, which are potentially thrombogenic. Therefore, we apply this method for evaluating the blood coagulation process spiked with fibrinogen.

We disclose an ARF-OCE system to detect and track the elastic properties by measuring the amplitude of vibration; resonant frequency of vibration and velocity of elastic wave in whole blood under static and flowing conditions. The vibration induced by ARF is measured by an OCT system. Then amplitude of vibration, resonant frequency of vibration and velocity of elastic wave is determined by OCT analysis methods. The coagulation metrics e.g. reaction time, clot formation kinetics, and maximum clot stiffness are produced.

An optical approach uses an acoustic radiation force (ARF) based optical coherence elastography (ARF-OCE), to rapidly assess dynamic whole blood coagulation by measuring the elastic properties of blood during coagulation. In this system, ARF excitation is produced by a remote ultrasonic transducer and vibration induced by ARF excitation is detected by an optical coherence tomography (OCT) system. During blood coagulation, changes in the elastic properties of the clot increase Young's modulus and shear modulus of samples and, thus, alter the propagating velocity of elastic wave, the amplitude of vibration and resonant frequency of vibration. As a result, the process and status during dynamic blood coagulation can be measured by relating the velocity of the elastic wave, the amplitude of vibration and the resonant frequency of vibration with clinically relevant coagulation metrics, e.g., reaction time, clot formation kinetics, and maximum elastic modulus (i.e. maximum clot stiffness). The ARF-OCE is sensitive to the clot formation kinetics and strength. The coagulation metrics e.g. reaction time, clot formation kinetics, and maximum clot stiffness are produced or derived from the measurements.

The potential applications of this invention include diagnosis and treatment management for bleeding patients in a variety of clinical situations in real-time at the point of care, assessment of hypo- and hyper-coagulatable states and monitoring of pharmacological treatment with anti- and procoagulant drugs.

The potential applications of this invention include diagnosis and treatment management for bleeding patients in a variety of clinical situations in real-time at the point of care, assessment of hypo- and hyper-coagulable states and monitoring of pharmacological treatment with anti- and procoagulant drugs.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations; but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The disclosure can be better visualized by turning now to the following drawings wherein like elements are referenced by like numerals.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1a and 1b show the OCT and Doppler variance images for the blood coagulation measurement. FIG. 1a is the OCT image at the beginning of the measurement. The ARF focus is moved downwards by a mechanical Z stage at a step of 1 mm for each measurement and the OCT M-scan is applied at the position indicated by the white arrow. FIG. 1b shows the Doppler variance images at four typical time points, 3, 8, 30 and 60 minutes, successively using the three ARF focus positions of FIG. 1a. In the process of blood coagulation, the wave occurrence time of the shear wave becomes shorter, indicating a faster shear wave velocity using each of the ARF focus positions.

FIG. 2a is a graph of the measured occurrence time of the shear wave at the wave detection point. Three ARF focus positions are applied for the measurement. FIG. 2b is a graph of the calculated shear wave velocity during blood coagulation. The increase of the shear wave velocity indicates the blood clot becoming stiffer. FIG. 2c is a graph of the shear modulus during blood coagulation. The shear modulus increases rapidly during the early stage of blood coagulation and becomes stable after 30 min. FIG. 2d is a graph of the relation between the shear wave velocity and the shear wave occurrence time at the wave detection point with the lower ARF focus excitation.

The disclosure and its various embodiments can now be better understood by turning to the following detailed description of the preferred embodiments which are presented as illustrated examples of the embodiments defined in the claims. It is expressly understood that the embodiments as defined by the claims may be broader than the illustrated embodiments described below.

DETAILED DESCRIPTION OF THE PREFERRED EMBODIMENTS

Figure 5:
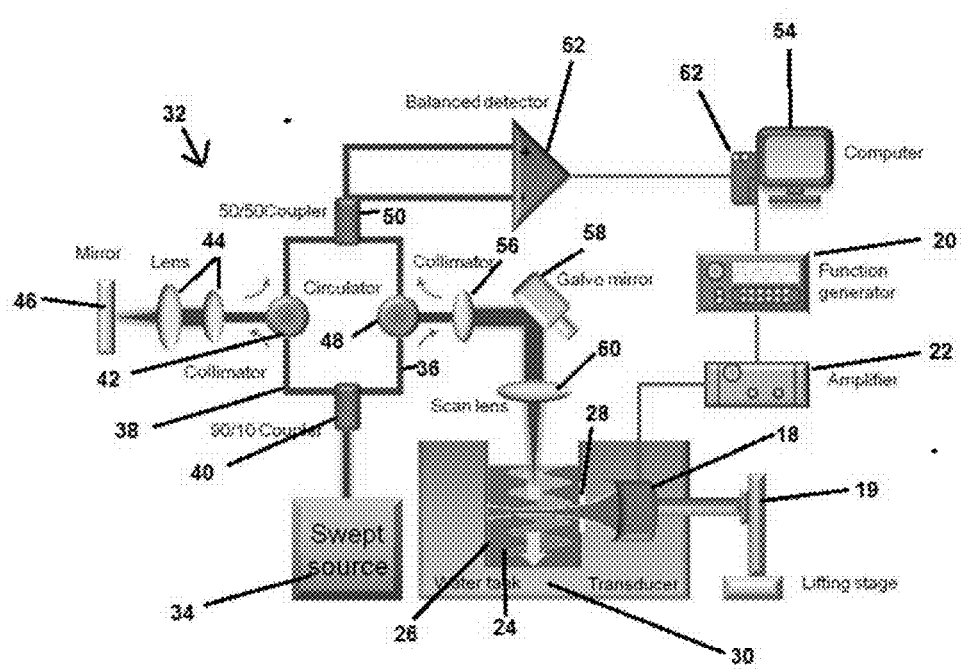
FIG. 5 is a schematic diagram of the ARFOE-OCE system, including the swept source OCT unit and ultrasonic excitation unit used to demonstrate the methodology of the disclosure. The vibration perpendicular to the OCT detection direction is detected by a Doppler variance method, and the shear wave propagating parallel to the OCT detection direction is measured by M-scans. The blood is disposed in a box with a window of plastic wrap for the ultrasound wave transmission. The box and the transducer are immersed in water for impedance matching of the ultrasound wave into the blood sample. Only the container contacts the blood sample.

Before considering the results of the study, turn to the ARFOE-OCE setup used to demonstrate the methodology. The experimental setup for the ARFOE-OCE is shown in FIG. 5. For ARF generation, an ultrasonic transducer 18 with a resonant frequency of 4.5 MHz is driven by the amplified sine wave at 160 V peak-to-peak using a function generator 20 and amplifier 22. The blood sample 24 is disposed in a box 26 with a window 28 of plastic wrap provided for the ultrasound wave transmission. The box 26 and the transducer 28 are immersed in water 30 for impedance matching of the ultrasound wave into the blood sample 24. The OCT system 32 is conventional and is based on a swept source 34 with a central wavelength of 1310 nm and an A-line speed of 50 kHz. The light from the swept laser source 34 is split into the sample arm 36 and the reference arm 38 with a power of 90% and 10% by 90/10 coupler 40, respectively. Reference arm 38 includes circulator 42, and lens system 44 coupling light to reference mirror 46. Sample arm 36 includes circulator 48 lens 56, galvo scanning mirror 58, and scanning lens 60. The reference and returned scattered light from blood sample 24 are returned to 50/50 coupler 50 and thence to balanced detector 52. The interference data output from detector 52 is provided is analog-to-digital converter 62 and software controlled computer 54 wherein the diagnosis process is controlled and wherein the data analysis and processing discussed below is performed.

For shear wave detection, 1000 A-lines at a rate of 50 kHz, corresponding to total time of 20.0 ms, are involved in one OCT M-scan, and the ARF excitation is applied between the 101st A-line to the 150th A-line corresponding to 1.0 ms emission. In this system, the ARF-induced vibration is perpendicular to the OCT beam, and the shear wave propagates along the OCT beam. Only the container or box 26 contacts the blood sample 24. The acoustic excitation system and optical detection system do not contact the blood sample 24.

Consider briefly the image acquisition and analysis. The fresh citrated whole blood sample 24 is placed in a container or box 26 opened with a thin-film window 28 through which the ultrasound passes. As whole blood is a highly scattering media and the OCT penetration depth is shallow in blood, it is difficult to visualize the shear wave propagation from the ARF focus to the sample surface. We use an alternative method to calculate the shear wave velocity, which is to measure the time delay of the shear wave propagating to the same depth after moving the ARF focus downwards to a known step by a mechanical Z stage 19.

As a feasibility test fresh porcine blood is anticoagulated with sodium citrate (Sierra for medical science, USA). To activate coagulation, the blood sample of 9.0 mL is recalcified by adding 1.0 mL calcium chloride (0.2 M). After 10 gentle vial inversions, the mixed whole blood is immediately loaded into the blood container 26 for the ARFOE-OCE dynamic measurements until 60 min.

A kaolin effect test is run using a saline solution of 360 μL added to 9 mL citrated porcine whole blood (Sierra for medical science. USA) without kaolin as the control group (n=3) and with 20 g/L kaolin as the treatment group (n=3). The mixtures are then triggered to clot by adding 530 μL calcium chloride (0.2 M). The occurrence time T of the shear wave is measured for 20 min during the coagulation of the blood with kaolin and for 30 min during the coagulation of the blood without kaolin which is enough time for the shear modulus to reach the plateau.

A fibrinogen effect test is run using a fibrinogen solution (50 g/L) prepared from fibrinogen powder (Sigma, USA) and saline and added to 9 mL citrated porcine whole blood (Sierra for medical science, USA), to increase fibrinogen level with 4 g/L from the initial concentration. One aliquot is mixed with saline as a control (n=3). The mixtures are then triggered to clot by adding 530 μL calcium chloride (0.2 M). ARFOE-OCE tests are performed using native whole blood (n=3) and whole blood spiked with fibrinogen (n=3). The occurrence time of the shear wave is measured for 30 min during the coagulation of the blood which is enough time for the shear modulus to reach the plateau.

Turn now to the methodology of the disclosed invention and the results obtained thereby. First, we investigate the feasibility of the ARFOE-OCE for measuring the shear modulus in the clotting blood. Time-course coagulation of the citrated porcine whole blood is investigated. FIG. 1a shows the OCT image in a B-mode at 3 min following the recalcification of blood coagulation. For the shear wave detection, 43 M-scans are captured at the position indicated by the white arrow 10 in FIG. 1a using each of three ARF excitation positions with a spacing of 1 mm. FIG. 1b shows the Doppler variance images at four typical e points successively using three ARF focus positions, namely upper focus 12, middle focus 14 and lower focus 16. At 3 min, no obvious vibration is detected; thus, no shear wave propagates to the OCT imaging area. After 8 min, the transverse vibration of the blood sample is detectable, which is generated by a shear wave propagating from the ARF focus. In the process of sampling time, the wave occurrence time becomes shorter, indicating a faster shear wave velocity using each of the ARF focus positions 12, 14 and 16.

Figure 2A:
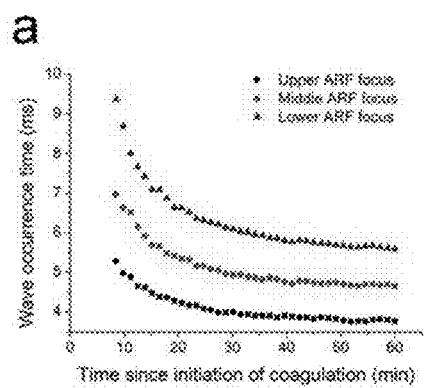
FIGS. 2a-2d illustrate the analysis of the shear wave during blood coagulation.
Figure 2B:
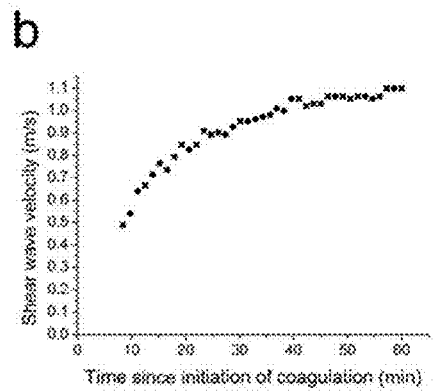
Figure 2C:
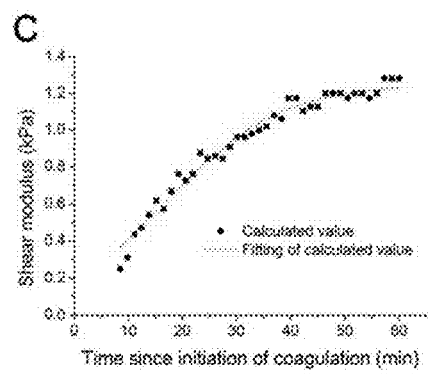
Figure 2D:
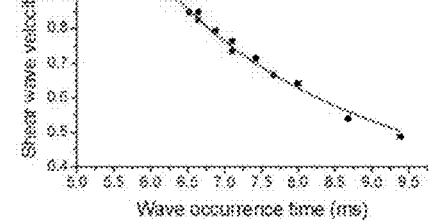

We determine the reaction time by detecting the vibration occurrence after the Doppler variance value is 0.025 a.u. larger than the background for the detected peak. The measured occurrence time of the shear wave is shown in FIG. 2a for the three positions 12, 14, and 16. When the ARF focus is moved downward at a spacing of 1 mm (that is, the ARF focus is moved away from the wave detection point), the wave occurrence time is delayed as shown in FIG. 2a. The average shear wave velocity can be calculated by the distance of two ARF focus positions and the time difference of wave occurrence. The calculated shear wave velocities during 60 min are shown in FIG. 2b, which are measured by the application of the upper ARF focus and lower ARF focus. The density of the porcine blood clot changes slightly during the measurement so an average density ρ of 1.06 kg/m³ is used in Eq. 1. The shear moduli during porcine whole blood coagulation are calculated by Eq. 1, as shown in FIG. 2c. The shear modulus increases rapidly during the early stage of blood coagulation and gradually reaches a plateau after 30 min. The shear modulus of the clotted blood at 46 min is 1.20 kPa as shown in FIG. 2c, which is close to the value 1.39 kPa measured by the MTS Synergie 100 mechanical test. FIG. 2d reveals a relation between the shear wave velocity V and the occurrence time T of the shear wave at the wave detection point with the lower ARF focus excitation, which can also be described by the following equation:

$$V = \frac{D}{T - T_0} \quad (2)$$

where D is the distance between the wave detection point and the ARF focus, and $T_0$ is the occurrence time of the shear wave at the ARF focus. The fitting of the data in FIG. 2d using Eq. 2 reveals the distance D and the occurrence time $T_0$; thus, the shear wave velocity can also be calculated by occurrence time T of the shear wave using Eq. 2.

In order to quantitatively characterize the elastic changes during blood coagulation, we developed coagulation metrics including the reaction time describing the earliest time when the shear wave is detectable, clot formation kinetics describing the clot formation rate, and maximum shear modulus describing the maximum clot firmness. According to a previous study on elastic dynamics, the change of the elastic modulus during blood coagulation can be modeled approximately by the logistic function, which is described by the following equation:

$$\mu = \frac{\mu_{max}}{1 + e^{-k(t-t_c)}} \quad (3)$$

where $\mu_{max}$ is the maximum shear modulus, t is the sampling time, k is the clot formation kinetics describing the clot formation rate, and $t_c$ is sampling time at the sigmoid's midpoint.

Once blood starts to clot, fibrin strands are formed, progressively increasing the firmness of the blood. FIG. 2c is presented as an elastic property tracing of clot formation, providing the information on clot formation kinetics and strength. Three distinct stages of the sample can be identified during coagulation. During the first stage, the blood is in a liquid state: there are no shear waves detectable. During the second stage, the blood progressively turns into a gel state because of the transformation of fibrinogen into fibrin through a coagulation cascade reaction. In this stage, the propagation velocity of the shear wave and, thus, the shear modulus, increases markedly with increasing firmness. In the third stage, the propagation velocity of the shear wave and, thus, the shear modulus, changes to a small extent with an approximate horizontal asymptote, corresponding to the stability and maximum firmness of the clot. Therefore, reaction time is defined as the time from the start of a sample run until the first detectable level of the shear wave in the Doppler variance image, similar to PT and aPTT. Clot formation kinetics k is defined as the clot formation rate and determined by Eq. 3 from the point of clot initiation to the peak strength of the clot. Maximum shear modulus represents the maximum clot firmness. This study demonstrates that the ARFOE-OCE is a feasible method for quantitatively analyzing the dynamic coagulation progress and status of whole blood.

Figure 3:
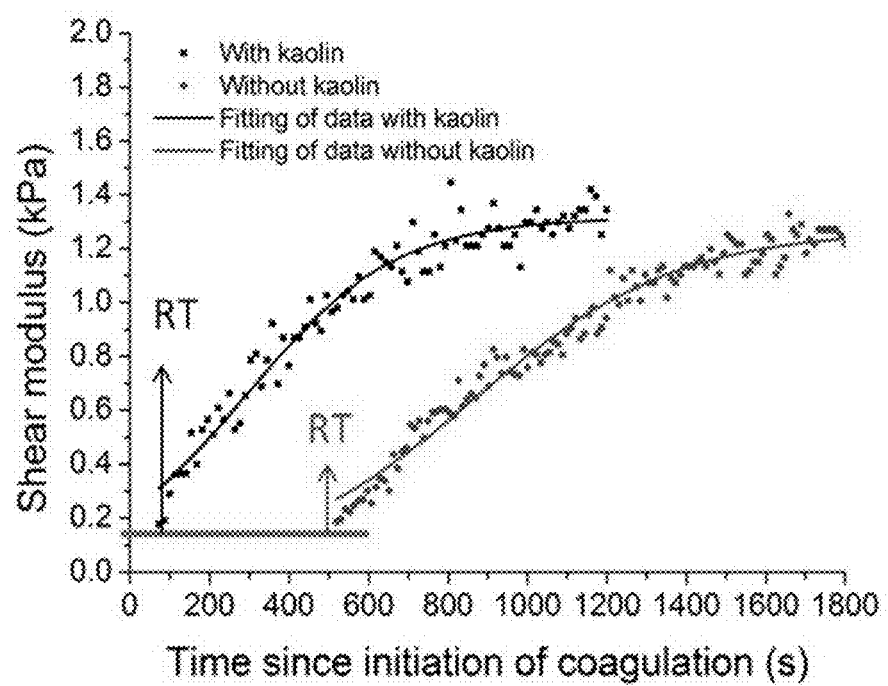
FIG. 3 is a graph providing a comparison of shear modulus change with and without the kaolin during porcine whole blood coagulation. The reaction time is significantly different between the sample with kaolin and the sample without kaolin. The presence of kaolin results in an earlier reaction time.

When TEG assay is performed, kaolin may be used as the factor XII (FXII) activator in order to facilitate the clot formation. Therefore, the capability of ARFOE-OCE for characterizing the different coagulation process activated by kaolin is evaluated and shown in FIG. 3. A saline solution is added to citrated porcine whole blood without kaolin as the control group (n=3) and with kaolin as the treatment group (n=3). There is a significant difference between the two groups of blood samples in the reaction time (P<0.01), and the presence of kaolin results in an earlier reaction time. The values of reaction time, clot formation kinetics and maximum shear modulus for two groups of blood samples are presented in Table 1 below. The presence of kaolin significantly influences the reaction time but not the clot formation rate or the peak firmness of clot (P>0.05).

A saline solution is added to citrated porcine whole blood without kaolin as the control group (n=3) and with kaolin as the treatment group (n=3). The presence of kaolin significantly influences the reaction time but not the clot formation rate or the peak firmness of clot. P-values are calculated by the T-test.

TABLE 1

Coagulation metrics for kaolin effect

| Sample type | Reaction Time Mean ± SD (s) | P-value | Maximum shear modulus Mean ± SD (kPa) | P-value | Clot formation kinetics Mean ± SD (1/s) | P-value |
|---|---|---|---|---|---|---|
| Group without kaolin | 472 ± 50 | P < 0.01 | 1.36 ± 0.08 | P > 0.05 | 0.0038 ± 0.0005 | P > 0.05 |
| Group with kaolin | 121 ± 41 | | 1.25 ± 0.16 | | 0.0049 ± 0.0007 | |

Figure 4:
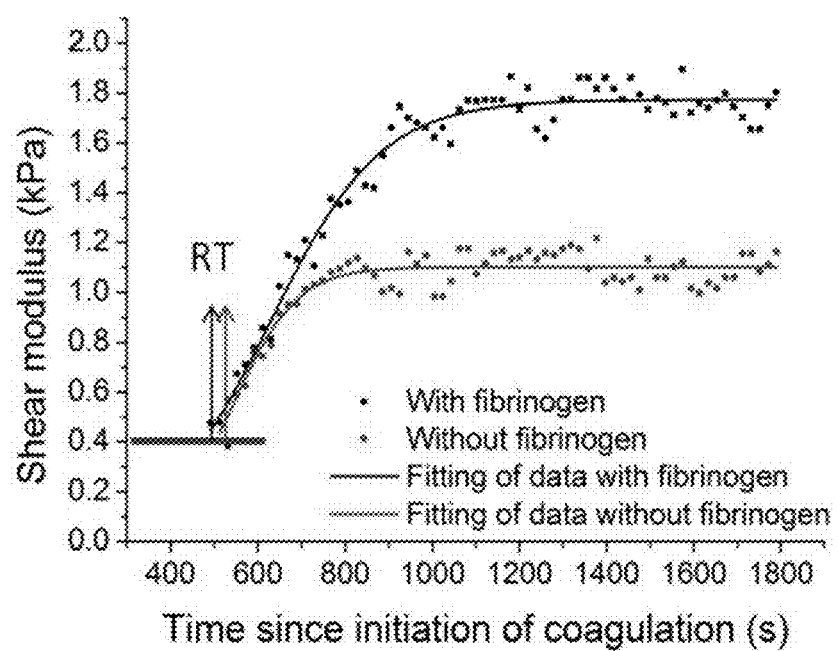
FIG. 4 is a graph 4 of the comparison of shear modulus change with and without the fibrinogen during porcine whole blood coagulation. The additional fibrinogen changes the clot formation rate and increases the clot stiffness. No significant difference in the reaction time is measured between the control group and group spiked with fibrinogen.

The capability of ARFOE-OCE for characterizing the different coagulation process spiked by fibrinogen is evaluated and shown in FIG. 4. The tests are performed using porcine whole blood without fibrinogen (n=3) and porcine whole blood spiked with fibrinogen (n=3). The addition of fibrinogen does not significantly affect the reaction time (P>0.05) but significant differences are observed between the control group and blood samples with additional 4 g/L fibrinogen in the clot formation kinetics (P<0.01) and maximum shear modulus (P<0.01), respectively. The values of reaction time, clot formation kinetics and maximum shear modulus for two groups of blood samples are presented in Table 2 below. The presence of additional fibrinogen significantly changes the clot formation rate and increases the peak firmness of clot.

ARFOE-OCE tests are performed using native whole blood (n=3) and whole blood spiked with fibrinogen (n=3). The presence of additional fibrinogen significantly changes the clot formation rate and increases the peak firmness of clot. P-values are calculated by the T-test.

TABLE 2

Coagulation metrics for fibrinogen effect.

| Sample type | Reaction Time | | Maximum shear modulus | | Clot formation kinetics | |
|---|---|---|---|---|---|---|
| | Mean ± SD (s) | P-value | Mean ± SD (kPa) | P-value | Mean ± SD (1/s) | P-value |
| Group without fibrinogen | 519 ± 30 | P > 0.05 | 1.17 ± 0.07 | P < 0.01 | 0.0135 ± 0.0009 | P < 0.01 |
| Group with fibrinogen | 538 ± 49 | | 1.69 ± 0.09 | | 0.0078 ± 0.0001 | |

To verify the method, we perform kaolin activating and fibrinogen spiking experiments by continuously recording the shear modulus during clot formation. The reaction time is significantly shortened after intrinsic activation with Kaolin, similar to the results from TEG measurement. Great changes in clot formation rate and clot firmness are evident after addition of fibrinogen. The results are in agreement with the measurement of FIBTEM MCF assessed by thromboelastometry. Similar to the FIBTEM MCF measurements, the changes in maximum shear modulus measured by ARFOE-OCE should not be considered as a measurement of fibrinogen concentration, but a measurement of mechanical properties of the fibrin clot.

The novel approach described here represents the first elastic coagulation test method capable of measuring whole blood coagulation metrics, such as reaction time, clot formation kinetics, and maximum shear modulus, by measuring the propagation velocity of the shear wave. The foundation of our approach is our new ARFOE-OCE incorporating the Doppler variance method capable of high-speed and high-sensitivity functional imaging; thus producing non-contact and rapid measurements of blood coagulation in real-time without subsequent calibration. We have tested three samples for each group in this study. Although large sample size test may be required for the clinical validation, our results demonstrated the capability of this method for measure the whole blood coagulation metrics.

Using our method, the clot development can be visually displayed in real-time as the shear wave propagates, and the blood clot elasticity can be simply and accurately measured. Blood clot elasticity is a potentially powerful metric for predicting the risk associated with the presence of blood clots. Abnormal clot elasticity is associated with myocardial infarction, coronary atherothrombosis, ischemic stroke, venous thromboembolism, and diabetes. The importance of dot elastic modulus is evidenced by the growing use of devices such as TEG. The coagulation metrics developed by our method are similar to TEG measurement, i.e., the time until initial fibrin formation (TEG®, reaction time; ROTEM®, clotting time [CT]), the kinetics of fibrin formation and clot development (TEG®, kinetics, α angle [α]; ROTEM®, clot formation time, α angle [α]), and the ultimate strength and stability of the fibrin clot (TEG®, maximum amplitude [MA]; ROTEM®, maximum clot firmness [MCF]). More than 3000 publications are related to the use of TEG methods, in both research and clinical/perioperative settings. However, TEG devices generate output by transducing changes in the viscoelastic strength of clotting blood to which a constant rotational force is applied. The rotation of the pin of TEG/ROTEM® begins to be impaired after fibrin-platelet bonding has linked the cup and pin together. Thus, the output is directly related to the strength of the formed clot. Unlike TEG techniques, the output of ARFOE-OCE is sensitive to elasticity and monitors elasticity changes that occur during initiation of coagulation and clot development. Therefore, the disclosed approach has the advantage of being an OCE Doppler variance method that has the potential for high accuracy. The high sensitivity of the OCT system provides typically microstrain sensitivity. Thus, our approach may overcome several limitations of both routine coagulation tests and TEG measurements.

Because of the noninvasive nature, this technology also has the potential to perform in vivo imaging. This technology will have significant impacts in clinical researches, disease diagnoses and treatment management for bleeding patients in a variety of clinical situations, assessment of hypo- and hyper-coagulable states, and monitoring of pharmacological treatment with anti- and procoagulant drugs.

Therefore in summary it can now be appreciated that the illustrated embodiments of the invention include an optical coherence elastography (OCE) method under acoustic radiation force (ARF) excitation to dynamically measure elastic properties of whole blood during coagulation and then assess the clot formation/dissolution kinetics and strength. The vibration in whole blood is induced by acoustic radiation force and is detected by an optical coherence tomography (OCT) method. The amplitude of vibration, resonant frequency of vibration and velocity of elastic wave are analyzed using OCT data for the measurement of elastic properties.

The optical coherence tomography (OCT) method may be a Doppler OCT phase method and a Doppler OCT variance method, as well as related OCT methods for the vibration detection.

The Doppler OCT variance method may be phase-resolved Doppler variance and intensity-based Doppler variance, as well as correlation-based methods.

Acoustic radiation force may be produced by an ultrasound transducer and a speaker.

The measurement parameters related to elastic properties of whole blood may be amplitude of vibration, resonant frequency of vibration and velocity of elastic wave The elastic wave propagating in whole blood may be a shear wave, a surface wave and a Lamb wave.

The resonant frequency of vibration may be determined by applying step frequency excitations and measuring corresponding vibration amplitude at each excitation frequency.

The amplitude of vibration may be measured by the displacement of tissue.

Elastic properties may be shear modulus, Young's modulus, velocity of shear wave, velocity of surface wave, velocity of Lamb wave and velocity of other elastic wave.

The coagulation metrics by the measurement of elastic properties may include reaction time describing the earliest time when the shear wave is detectable, clot formation kinetics describing the clot formation rate, and maximum shear modulus describing the maximum clot stiffness.

During clot formation/dissolution, whole blood may be under static conditions and under flowing conditions.

The elastic measurement may be performed in vivo and in vitro.

The amplitude of vibration induced by ARF is measured to assess the elastic properties during clot formation/dissolution under static and flowing conditions of whole blood.

The resonant frequency of vibration induced by ARF is measured to assess the elastic properties during clot formation/dissolution under static and flowing conditions of whole blood.

The velocity of elastic wave induced by ARF is measured to assess the elastic properties during clot formation/dissolution under static and flowing conditions of whole blood.

The elastic properties of whole blood during clot formation/dissolution under static and flowing conditions may include shear modulus, Young's modulus, velocity of shear wave, velocity of surface wave, velocity of Lamb wave and velocity of other elastic wave.

ARF-induced vibration in whole blood during clot formation/dissolution under static and flowing conditions may be detected by a Doppler OCT phase method, or a Doppler OCT variance method, as well as related OCT methods.

This method may provide a visual assessment of clot formation and subsequent analysis of whole blood under static and flowing conditions.

This method may allow the process of clot initiation, propagation, stabilization, and dissolution of whole blood under static and flowing conditions to be evaluated separately.

This method may provide information on the interactions of coagulation factors, inhibitors, red blood cells, platelets, and anticoagulants during clot formation and subsequent fibrinolysis hole blood under static and flowing conditions.

Compared to the standard laboratory coagulation tests (i.e. PT, aPTT, fibrinogen level, platelet level) with long turnaround times and of limited value in perioperative and acutely ill patient, the illustrated embodiment provides rapid, dynamic, visual assessment that creates the unique opportunity for evaluating a patient's coagulation status in real-time at the point of care.

Compared to TEG and the modified rotational TEG (ROTEM) that involve mechanically stirring blood and measuring changes in blood viscoelastic properties during clotting, the illustrated embodiment, a noncontact technique, is superior to the contact techniques in terms of sensitivity, repeatability, and standardization.

Many alterations and modifications may be made by those having ordinary skill in the art without departing from the spirit and scope of the embodiments. Therefore, it must be understood that the illustrated embodiment has been set forth only for the purposes of example and that it should not be taken as limiting the embodiments as defined by the following embodiments and its various embodiments.

Therefore, it must be understood that the illustrated embodiment has been set forth only for the purposes of example and that it should not be taken as limiting the embodiments as defined by the following claims. For example, notwithstanding the fact that the elements of a claim are set forth below in a certain combination, it must be expressly understood that the embodiments includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the embodiments is explicitly contemplated as within the scope of the embodiments.

The words used in this specification to describe the various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the embodiments.

We claim:

1. A method of using an optical coherence elastography (OCE) under acoustic radiation force (ARF) excitation comprising:
   inducing a shear wave in a blood sample by use of an ultrasound beam from an ultrasonic transducer;
   measuring an elastic property of the blood sample by use of an optical coherence tomography (OCT) beam; and
   assessing the clot formation/dissolution kinetics and strength,
   wherein the OCT beam is orientated orthogonally relative to the ultrasound beam to dynamically measure the shear wave in the blood sample during coagulation.

2. The method of claim 1 where inducing the shear wave in the blood sample comprises inducing vibration in the blood sample by acoustic radiation force and where measuring the elastic property of the blood sample comprises detecting the vibration by an optical coherence tomography (OCT) to determine the amplitude of vibration, resonant frequency of vibration, and velocity of an elastic wave.

3. The method of claim 1 where measuring an elastic property of the blood sample by use of an optical coherence tomography (OCT) beam comprises measuring the elastic property of the blood sample by use of a Doppler OCT phase method or a Doppler OCT variance method.

4. The method of claim 2 where detecting the vibration by an optical coherence tomography (OCT) comprises measuring the amplitude of vibration by measuring the displacement of tissue.

5. The method of claim 2 where detecting the vibration by an optical coherence tomography (OCT) comprises determining the resonant frequency of the vibration by applying step frequency excitations and measuring corresponding vibration amplitude at each excitation frequency.

6. The method of claim 3 where the Doppler OCT variance method comprises a phase-resolved Doppler variance, intensity-based Doppler variance, or a correlation-based method.

7. The method of claim 1 further comprising inducing a surface wave or a Lamb wave.

8. The method of claim 1 where measuring an elastic property of the blood sample comprises measuring shear modulus, Young's modulus, velocity of shear wave, velocity of surface wave, velocity of Lamb wave or velocity of another elastic wave.

9. The method of claim 1 where measuring an elastic property of the blood sample comprises measuring reaction time describing the earliest time when the shear wave is detectable, clot formation kinetics describing the clot formation rate, or maximum shear modulus describing the maximum clot stiffness.

10. The method of claim 1 where measuring the elastic property of the blood sample comprises measuring the elastic property during clot formation/dissolution under static conditions or under flowing conditions.

11. An apparatus for measuring an elastic property of a blood sample during coagulation comprising:
an optical coherence elastography (OCE) system for measuring the elastic property of the blood sample;
an ultrasound generator for applying acoustic radiation force (ARF) excitation to the blood sample,
where the acoustic radiation force (ARF) induces an ultrasound shear wave in the blood sample,
where the optical coherence elastography (OCE) system generates an optical coherence tomography (OCT) wave orthogonal to the ultrasound wave to dynamically measure the elastic property of the blood sample during coagulation and receives an optical coherence tomographic response from the acoustic radiation force (ARF) excited blood sample; and
a processor which dynamically assesses clot formation/dissolution kinetics and strength from the optical coherence tomographic response from the acoustic radiation force (ARF) excited blood sample.

12. The apparatus of claim 11 where the optical coherence elastography (OCE) system measures amplitude of vibration, resonant frequency of vibration, and velocity of an elastic wave induced by the ultrasound generator.

13. The apparatus of claim 12 where the optical coherence elastography (OCE) system measures resonant frequency of vibration by applying step frequency excitations and measuring corresponding vibration amplitude at each excitation frequency.

14. The apparatus of claim 12 where the optical coherence elastography (OCE) system measures the amplitude of vibration by measuring the displacement of tissue.

15. The apparatus of claim 11 where the optical coherence elastography (OCE) system comprises a Doppler OCT phase apparatus or a Doppler OCT variance apparatus.

16. The apparatus of claim 15 where the Doppler OCT variance apparatus comprises a phase-resolved Doppler variance apparatus, intensity-based Doppler variance apparatus, or a correlation-based apparatus.

17. The apparatus of claim 11 where the ultrasound generator is configured to induce a surface wave or a Lamb wave.

18. The apparatus of claim 11 where the optical coherence elastography (OCE) system measures shear modulus, Young's modulus, velocity of shear wave, velocity of surface wave, velocity of Lamb wave or velocity of another elastic wave.

19. The apparatus of claim 11 where the optical coherence elastography (OCE) system measures reaction time describing the earliest time when the shear wave is detectable, clot formation kinetics describing the clot formation rate, or maximum shear modulus describing the maximum clot stiffness.

20. The apparatus of claim 11 where the optical coherence elastography (OCE) system measures the elastic property during clot formation/dissolution under static conditions or under flowing conditions.

* * * * *